(12) United States Patent
Liu et al.

(10) Patent No.: US 10,528,809 B2
(45) Date of Patent: Jan. 7, 2020

(54) IRIS IMAGE CAPTURING DEVICE, IRIS IMAGE RECOGNITION DEVICE AND METHOD THEREOF

(71) Applicant: REALTEK SEMICONDUCTOR CORP., Hsinchu (TW)

(72) Inventors: Kai Liu, Taipei (TW); Wen-Tsung Huang, Chiayi (TW)

(73) Assignee: REALTEK SEMICONDUCTOR CORP., Hsinchu (TW)

( * ) Notice: Subject to any disclaimer, the term of this patent is extended or adjusted under 35 U.S.C. 154(b) by 152 days.

(21) Appl. No.: 15/867,367

(22) Filed: Jan. 10, 2018

(65) Prior Publication Data
US 2018/0232576 A1    Aug. 16, 2018

(30) Foreign Application Priority Data
Feb. 15, 2017    (TW) ............................. 106104894 A

(51) Int. Cl.
| G06K 9/00 | (2006.01) |
| G06F 21/32 | (2013.01) |
| A61B 3/14 | (2006.01) |
| A61B 5/1171 | (2016.01) |
| A61B 5/16 | (2006.01) |

(52) U.S. Cl.
CPC ............ *G06K 9/00604* (2013.01); *A61B 3/14* (2013.01); *A61B 5/1171* (2016.02); *G06F 21/32* (2013.01); *G06K 9/0061* (2013.01); *A61B 5/163* (2017.08); *G06K 9/00281* (2013.01); *G06K 9/00597* (2013.01); *G06K 9/00617* (2013.01); *G06T 2207/30041* (2013.01)

(58) Field of Classification Search
CPC .......... G06K 9/00604; G06K 9/00597; G06K 9/0061; G06K 9/00617; G06K 9/00281; G02B 27/0093; G06F 21/32; G06F 3/013; G06T 2207/30041
See application file for complete search history.

(56) References Cited

U.S. PATENT DOCUMENTS

| 2004/0153649 | A1* | 8/2004 | Rhoads ................. G06F 17/241 713/176 |
| 2017/0103261 | A1* | 4/2017 | Rauhala ............ G06K 9/00597 |
| 2018/0018516 | A1* | 1/2018 | Odinokikh ......... G06K 9/00604 |
| 2018/0160079 | A1 | 6/2018 | Huang et al. |

FOREIGN PATENT DOCUMENTS

| TW | I471808 B | 2/2015 |
| WO | WO 2013/109295 A2 | 7/2013 |

* cited by examiner

*Primary Examiner* — Ross Varndell
(74) *Attorney, Agent, or Firm* — Li & Cai Intellectual Property (USA) Office

(57) ABSTRACT

An iris image capturing device, an iris image recognition device and an iris image recognition method are provided. Multiple data sequences are captured, in which each data sequence includes an iris image. These data sequences are selected to be a positioning image or an image to be processed. The positioning image is for locating the iris, and the image to be processed is for generating a protected iris image according to where the iris is located in the positioning image.

17 Claims, 4 Drawing Sheets

IRIS IMAGE CAPTURING DEVICE, IRIS IMAGE RECOGNITION DEVICE AND METHOD THEREOF

BACKGROUND OF THE INVENTION

1. Field of the Invention

The present disclosure relates to an iris image capturing device, an iris image recognition device and an iris image recognition method; in particular, to an iris image capturing device, an iris image recognition device and an iris image recognition method that can protect iris features from interception.

2. Description of Related Art

The iris recognition technology is ranked at a high security level among biological recognition technologies. Everyone's iris is unique, and one's iris features do not change with age. Thus, compared with other biological recognition technologies, such as the fingerprint recognition technology or the face recognition technology, the iris recognition technology has higher uniqueness. Generally, an iris recognition system includes an image capturing device (such as a camera device) and an image processor (such as a computer system). The image capturing device is configured to capture an image having iris features and to transmit this image to the image processor in a wired or wireless way. Then, the image processor captures the iris features from the image and conducts iris recognition.

However, it is possible that, during data transmission, those with malevolent intentions may successfully intercept the image having one's iris features. Therefore, if the image having one's iris features can be protected from interception during the data transmission, the iris recognition technology can be safer.

SUMMARY OF THE INVENTION

The present disclosure provides an iris image capturing device, an iris image recognition device and an iris image recognition method. The present disclosure generates multiple data sequences that include an iris image, selects a certain data sequence as the positioning image, and selects other data sequences as images to be processed. The positioning image is used for locating the iris, and the image to be processed is used for generating a protected iris image according to where the iris is located in the positioning image. In this manner, the image having the iris features cannot be intercepted during the data transmission by those with malevolent intentions, thus rendering the iris recognition technology even safer.

The iris image capturing device provided by the present disclosure is used for capturing an iris image to protect the iris image, and includes an image sensor, a digital signal processor and a feature analyzer. The digital signal processor is connected to the digital signal processor, and the feature analyzer is connected to the digital signal processor. The image sensor captures an image of a scene in front of the image sensor to sequentially generate multiple data sequences. Each data sequence includes the iris image. The digital signal processor selects a first data sequence among the data sequences as a positioning image, and then lowers the resolution of the positioning image to generate a low-resolution image. After receiving the low-resolution image, the feature analyzer calculates a set of coordinates of the iris image in the low-resolution image, and transmits the set of coordinates of the iris image to the digital signal processor. After receiving the set of coordinates of the iris image, the digital signal processor selects a second data sequence among the data sequences as an image to be processed. In addition, according to the coordinates of the iris image, the digital signal processor captures, compresses and encrypts the iris image in the image to be processed to generate and transmit a protected iris image to the feature analyzer.

The iris image recognition device provided by the present disclosure includes an image sensor, a digital signal processor, a feature analyzer and an iris recognizer. The digital signal processor is connected to the image sensor, the feature analyzer is connected to the digital signal processor, and the iris recognizer is connected to the feature analyzer. The image sensor captures an image of a scene in front of the image sensor to sequentially generate multiple data sequences. Each data sequence includes an iris image. The digital signal processor selects a first data sequence among the data sequences as a positioning image, and then lowers the resolution of the positioning image to generate a low-resolution image. After receiving the low-resolution image, the feature analyzer calculates a set of coordinates of the iris image in the low-resolution image, and transmits the set of coordinates of the iris image to the digital signal processor. After receiving the set of coordinates of the iris image, the digital signal processor selects a second data sequence among the data sequences as an image to be processed. According to the set of coordinates of the iris image, the digital signal processor captures, compresses and encrypts the iris image in the image to be processed to generate a protected iris image. In addition, the digital signal processor transmits the protected iris image to the feature analyzer. After receiving the protected iris image from the feature analyzer, the iris recognizer decrypts and decompresses the protected iris image to generate a decompressed iris image. Then, the iris recognizer determines whether the decompressed iris image is an authorized image.

The iris image recognition method provided by the present disclosure is applied to an iris image recognition device. This iris image recognition method includes the following steps. Step 1: capturing an image of a scene in front of the iris image capturing device to sequentially generate multiple data sequences. In step 1, each data sequence includes the iris image. Step 2: selecting a first data sequence among the data sequences as a positioning image and lowering the resolution of the positioning image to generate a low-resolution image. Step 3: calculating a set of coordinates of the iris image in the low-resolution image. Step 4: selecting a second data sequence among the data sequences as an image to be processed, and according to the coordinates of the iris image, capturing, compressing and encrypting the iris image in the image to be processed to generate a protected iris image. Step 5: decrypting and decompressing the protected iris image to generate a decompressed iris image, and determining whether the decompressed iris image is an authorized image.

For further understanding of the present disclosure, reference is made to the following detailed description illustrating the embodiments of the present disclosure. The description is only for illustrating the present disclosure, not for limiting the scope of the claim.

BRIEF DESCRIPTION OF THE DRAWINGS

Embodiments are illustrated by way of example and not by way of limitation in the figures of the accompanying drawings, in which like references indicate similar elements and in which.

DETAILED DESCRIPTION OF EXEMPLARY EMBODIMENTS

The aforementioned illustrations and following detailed descriptions are exemplary for the purpose of further explaining the scope of the present disclosure. Other objectives and advantages related to the present disclosure will be illustrated in the subsequent description and appended drawings.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

Figure 1:
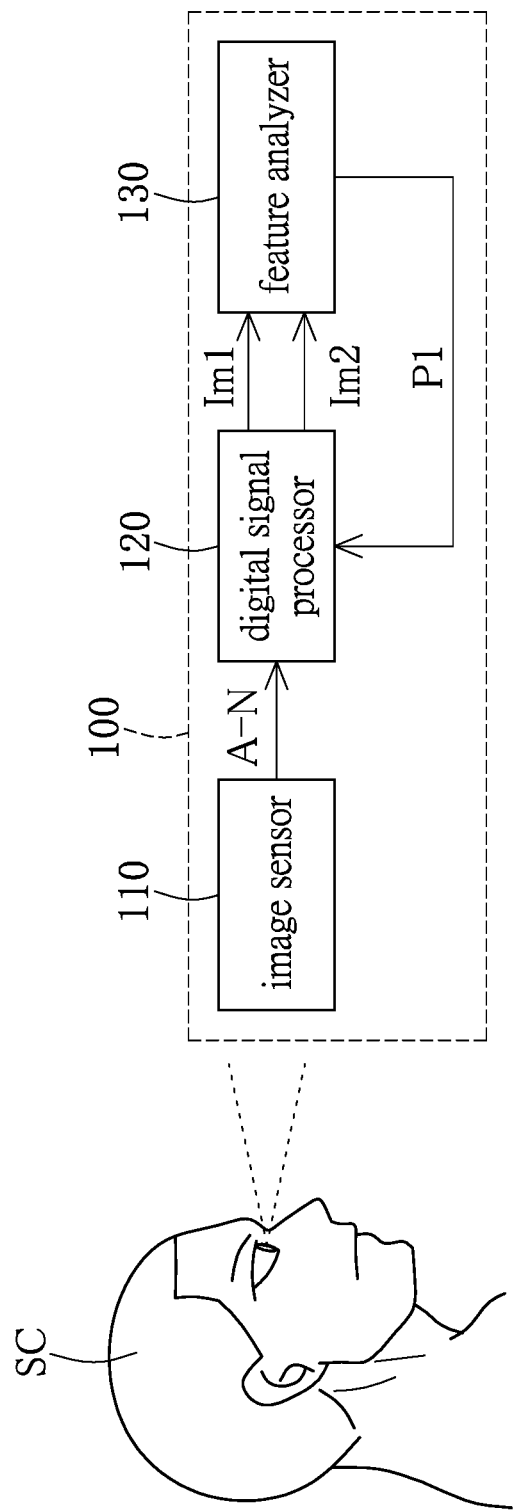
FIG. 1 shows a schematic diagram of an iris image capturing device according to one embodiment of the present disclosure.

Referring to FIG. 1, a schematic diagram of an iris image capturing device of one embodiment of the present disclosure is shown. The iris image capturing device 100 captures an iris image having iris features for protecting the captured iris image. The iris image capturing device 100 can protect the iris image from intercepting during a wired data transmission (such as the data transmission through a USB interface or a MIPI interface) or a wireless data transmission by those with malevolent intentions, thus rendering the iris recognition technology even safer.

As shown in FIG. 1, the iris image capturing device 100 includes an image sensor 110, a digital signal processor 120 and a feature analyzer 130. For example, the image sensor 110 and the digital signal processor 120 can be integrated as a camera module, and the feature analyzer 130 can be configured in a computer host and can be implemented by a firmware. In this example, the camera module transmits an image having iris features to the computer host in a wired or wireless way, and thus the computer host can proceed to process this image. In the following description, the connection relationship among the image sensor 110, the digital signal processor 120 and the feature analyzer 130 is illustrated, and the operating mechanism of the image sensor 110, the digital signal processor 120 and the feature analyzer 130 is also illustrated.

The image sensor 110 captures an image of a scene SC in front of the image sensor 110 to sequentially generate a plurality of data sequences. These data sequences are transmitted to the digital signal processor 120, and each data sequence includes the iris image. Specifically, the image sensor 110 continuously captures the image of the scene SC during a period of time, and converts the image of the scene SC to a plurality of data sequences. It should be noted that, iris features of a user are shown in the scene SC. In this embodiment, the iris image is an image of a human eye. In other embodiments, the iris image can be an image of an eye ball or an image of other parts of a human eye. The following description illustrates how the data sequences are generated.

Figure 2:
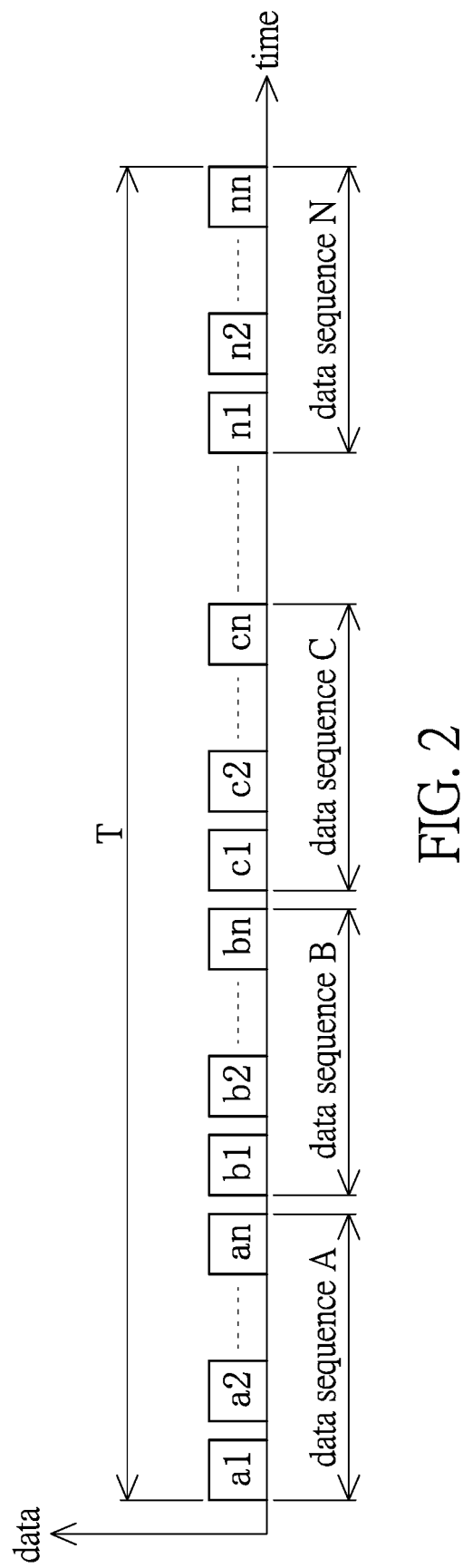
FIG. 2 shows the time sequences of the data sequences in one embodiment of the present disclosure.

Referring to FIG. 2, time sequences of the data sequences are shown. According to FIG. 2, the image sensor 110 continues to capture an image of a scene SC during a period of time T to generate a plurality of data sequences A, B, C . . . , N. Each of the data sequences A-N is the image data of one frame, and each of the data sequences A-N includes the iris image. When a user stands in front of the image sensor 110, the image sensor 110 continually captures an image having the user's iris features during a period of time T to generate a plurality of data sequences A-N. Each of the data sequences A-N is the image data of one frame, and each of the data sequences A-N includes the user's iris features. In addition, each of the data sequences A-N is consisted of a plurality of pixel data. For example, the data sequence A comprises pixel data a1, a2, . . . , an, the data sequence B comprises pixel data b1, b2, . . . , bn, the data sequence C comprises pixel data c1, c2, . . . , cn, and the data sequence N comprises pixel data n1, n2, . . . , nn. During the data transmission, the image sensor 110 sequentially transmits the pixel data a1, a2, . . . , an (which are the data sequence A), the pixel data b1, b2, . . . , bn (which are the data sequence B), the pixel data c1, c2, . . . , cn (which are the data sequence C), . . . , and the pixel data n1, n2, . . . , nn (which are the data sequence N) to the digital signal processor 120.

As shown in FIG. 1, the digital signal processor 120 is connected to the image sensor 110. The image sensor 110 selects one of the data sequences A-D to be a positioning image. For example, the digital signal processor 120 can select the first data sequence (in FIG. 2, the first data sequence is the data sequence A) among the data sequences to be the positioning image. Then, the digital signal processor 120 lowers the resolution of the positioning image to generate a low-resolution image Im1, and transmits the low-resolution image Im1 to the feature analyzer 130. It should be noted that, the low-resolution image Im1 is only generated for the feature analyzer 130 to determine where the human eye is, so that not many image details are required. Thus, in this embodiment, the low-resolution image Im1 is set as a 160*120 image for saving bandwidth during the data transmission, but the image size of the low-resolution image Im1 is not thus limited.

The feature analyzer 130 is connected to the digital signal processor 120 for receiving the low-resolution image Im1. The feature analyzer 130 calculates a set of coordinates P1 marking where the iris image is in the low-resolution image Im1, and transmits this set of coordinates P1 to the digital signal processor 120. The set of coordinates P1 refers to the position of the iris image in the low-resolution image Im1, and thus the digital signal processor 120 can find the iris images included in other data sequences according to the set of coordinates P1. Those skilled in the art should be equipped with knowledge on how to calculate the set of coordinates P1 of the iris image according to general knowledge of image processing, and thus details on how to calculate the set of coordinates P1 of the iris image are omitted.

After receiving the set of coordinates P1 of the iris image, the digital signal processor 120 selects another data sequence to be an image to be processed. In one example, the digital signal processor 120 selects the second data sequence (in FIG. 2, the second data sequence can be the data sequence B, C and/or D) among the data sequences to be the image to be processed, and then captures the iris image in the images to be processed according to the set of coordinates P1 of the iris image. For different purposes, the digital signal processor 120 processes the iris images in different ways. In one example, the digital signal processor 120 adjusts the exposure of the iris image and/or the contrast ratio of the iris image to emphasize the iris features in the iris image, but is not limited thereto. In this embodiment, the data sequence including the positioning image and the data sequence including the image to be processed are two adjacent data sequences. For example, in FIG. 2, these two data sequences can be the data sequence A and the data sequence B, or the data sequence B and the data sequence C. In another embodiment, the data sequence including the positioning image and the data sequence including the image to be processed can be two data sequences that are not adjacent to each other. For example, in FIG. 2, these two data sequences can be the data sequence A and the data sequence C.

After obtaining the iris image in the image to be processed, the digital signal processor 120 compresses and encrypts the iris image so as to generate a protected iris image Im2. This protected iris image Im2 is transmitted to the feature analyzer 130. The digital signal processor 120 can compress the iris image by using JPEG compression, Fixed Length Code (FLC) or other data compression technologies to downsize the data of the iris image. In this manner, the digital signal processor 120 can transmit more data to the feature analyzer 130. The digital signal processor 120 can encrypt the compressed iris image by the Advanced Encryption Standard (AES) algorithm or other kinds of algorithms to protect the iris features from intercepting when the digital signal processor 120 transmits image data to the feature analyzer 130 in a wired or wireless way.

Since the protected iris image Im2 is for recognizing the iris, more image details are required. To obtain more image details, the size of the protected iris image Im2 should be larger than the size of the low-resolution image Im1. Preferably, the size of the protected iris image Im2 can be 640*360 to ensure that sufficient iris features can be provided, but the size of the protected iris image Im2 is not thus restricted. In addition, the protected iris image Im2 can be consisted of an image of one eye and an image of the other eye, and the size of each image is 640*360.

When the iris image capturing device 100 transmits the protected iris image Im2 (specifically, when the digital signal processor 120 transmits the protected iris image Im2 to the feature analyzer 130 in a wired or wireless way), those with malevolent intentions cannot intercept iris features from the protected iris image Im2 due to the encryption of the protected iris image Im2. Thus, the iris image capturing device 100 provided by this embodiment makes the iris recognition technology even safer. Moreover, the digital signal processor 120 will locate the position of the iris image according to the set of coordinates P1 of the iris image to process the iris image in advance for the subsequent iris recognition procedure.

After receiving the protected iris image Im2, the feature analyzer 130 can directly determine whether the protected iris image Im2 is an authorized image, or can process the protected iris image Im2 for other purposes.

Figure 3:
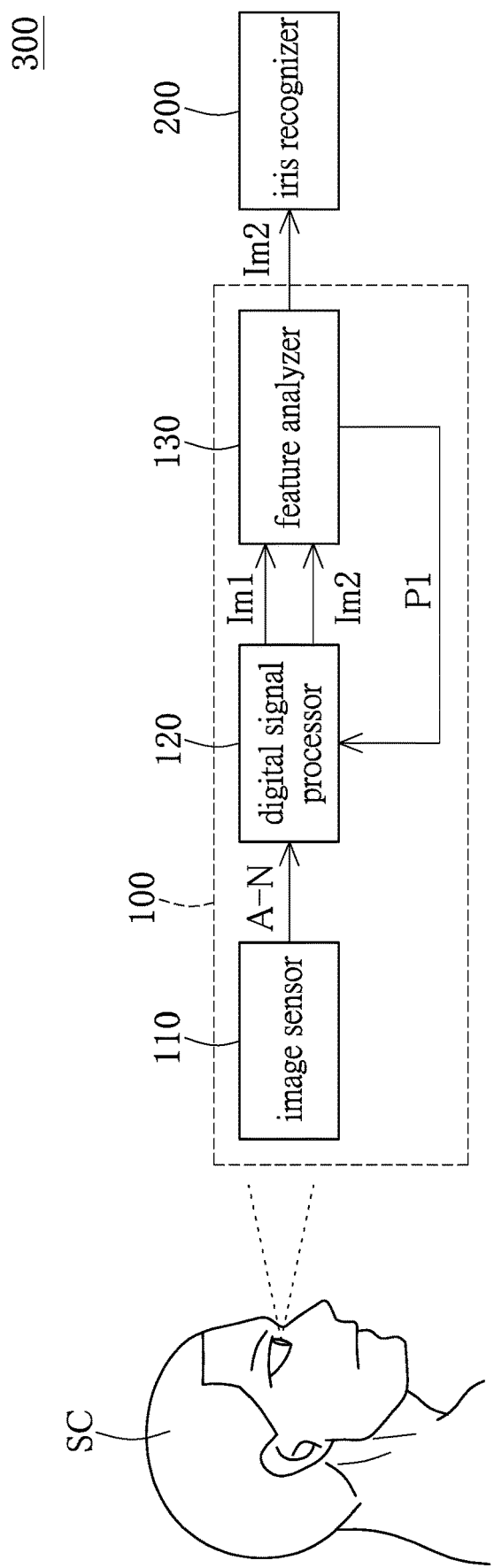
FIG. 3 shows a schematic diagram of an iris image recognition device of one embodiment of the present disclosure.

The iris image recognition device 300 is illustrated by an embodiment provided in the following description. Referring to FIG. 3, a schematic diagram of an iris image recognition device of one embodiment of the present disclosure is shown. According to FIG. 3, the iris image recognition device 300 includes an iris image capturing device 100 and an iris recognizer 200. The iris image recognition device 300 recognizes whether a received iris image is an authorized image. Details on the iris image capturing device 100 are provided in the above description, and thus are omitted hereinafter. The iris recognizer 200 is connected to the feature analyzer 100 to receive the protected iris image Im2 from the feature analyzer 100, and then to recognize the protected iris image Im2.

After receiving the protected iris image Im2, the iris recognizer 200 decrypts and decompresses the protected iris image Im2 to generate a decompressed iris image. It should be noted that, the way the protected iris image Im2 is decompressed corresponds to the way the iris image is compressed (for example, if the iris image is compressed using Fixed Length Code (FLC), the protected iris image Im2 should be decompressed using Fixed Length Code (FLC), and the way the protected iris image Im2 is decrypted corresponds to the way the iris image is encrypted (for example, if the iris image is encrypted using the AES algorithm, the protected iris image Im2 should be decrypted using AES algorithm). Additionally, the feature analyzer 130 of the iris image capturing device 100 and the iris recognizer 200 can both be configured in a computer host, or the iris image capturing device 100 can be remotely connected to the iris recognizer 200.

The iris recognizer 200 determines whether the decompressed iris image is an authorized image. In this embodiment, the authorized image maps to a unique code, and this unique code is stored in the iris recognizer 200. Specifically, the unique code is pre-stored in the iris recognizer 200, and this unique code corresponds to the iris features of a certain user. The decompressed iris image can be mapped to a code, and when this code is identical to the unique code, the iris recognizer 200 determines that the decompressed iris image is the authorized image. In other words, when this code is identical to the unique code, the iris image captured by the image sensor is the same as the authorized image. Additionally, when the iris recognizer 200 determines that the decompressed iris image is the authorized image, the iris recognizer 200 can correspondingly display a welcome message, such as "authorized identity", but it is not limited thereto. Moreover, the iris recognizer 200 can be implemented by hardware or software.

It is worth mentioning that the iris image cannot be recovered even when one acquires the unique code from the iris recognizer 200, thus ensuring that the user's iris features will not be stolen by those with malevolent intentions, and the user's iris features can be kept under a high level of protection.

Figure 4:
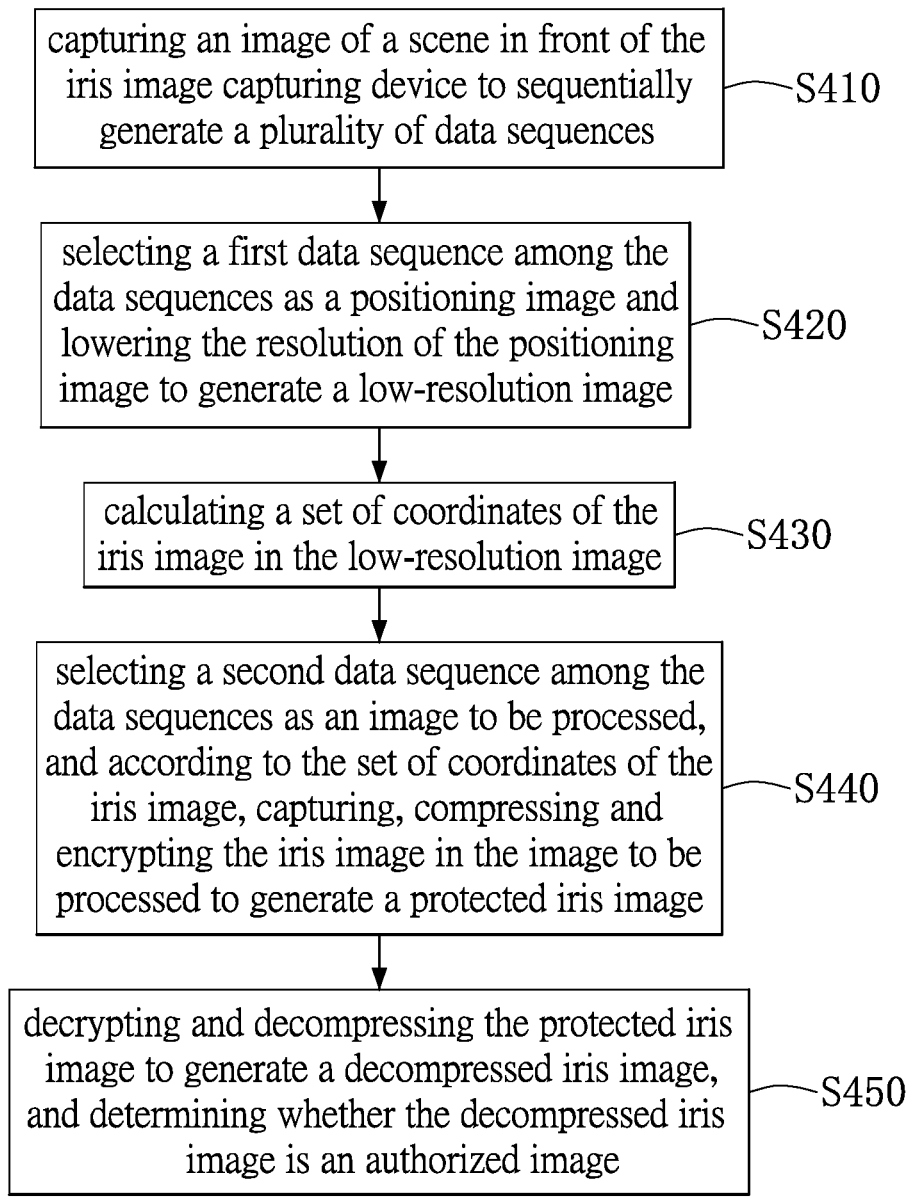
FIG. 4 shows a flow chart of an iris image recognition method of one embodiment of the present disclosure.

According to the iris image capturing device 100 and the iris image recognition device 300 provided in the above embodiments, an iris image recognition method is further provided by the present disclosure. This iris image recognition method can be applied to the iris image capturing device 100 and the iris image recognition device 300. Referring to FIG. 4, a flow chart of an iris image recognition method of one embodiment of the present disclosure is shown.

To begin with, the iris image recognition device 300 captures an image of a scene in front of the iris image capturing device 300 to sequentially generate a plurality of data sequences (step S410). In step S410, each data sequence includes the iris image.

The iris image recognition device 300 selects a first data sequence among the data sequences as a positioning image, and lowers the resolution of the positioning image to generate a low-resolution image (step S420). Then, the iris image recognition device 300 calculates a set of coordinates of the iris image in the low-resolution image (step S430).

After that, the iris image recognition device 300 selects a second data sequence among the data sequences as an image to be processed, and according to the set of coordinates of the iris image in the low-resolution image, the iris image recognition device 300 captures, compresses and encrypts the iris image in the image to be processed to generate a protected iris image (step S440).

Finally, the iris image recognition device 300 decrypts and decompresses the protected iris image to generate a decompressed iris image, and the iris image recognition device 300 determines whether the decompressed iris image is an authorized image (step S450). It is worth mentioning that, a unique code which the authorized image is mapped to is stored in the iris image recognition device 300. When a code that the decompressed iris image is mapped to is identical to the unique code, the iris image recognition device 300 determines that the decompressed iris image is an authorized image. On the other hand, when the code that the decompressed iris image is mapped to is not identical to the unique code, the iris image recognition device 300 determines that the decompressed iris image is not an authorized image.

Since details on the iris image recognition device 300 are provided in the above description, further details thereon are omitted hereinafter. By using the iris image capturing device, the iris image recognition device and the iris image recognition method provided by the present disclosure, a plurality of data sequences including the iris image are captured, and these data sequences are selected to be a positioning image or an image to be processed. The positioning image is for locating the iris, and the image to be processed is for generating a protected iris image according to the position of the iris in the positioning image. By using the iris image capturing device, the iris image recognition device and the iris image recognition method provided by the present disclosure, the image including iris features will not be intercepted by those with malevolent intentions during data transmission, thus rendering the iris recognition technology even safer.

The descriptions illustrated supra set forth simply the preferred embodiments of the present disclosure; however, the characteristics of the present disclosure are by no means restricted thereto. All changes, alterations, or modifications conveniently considered by those skilled in the art are deemed to be encompassed within the scope of the present disclosure delineated by the following claims.

What is claimed is:

1. An iris image capturing device, used for capturing an iris image to protect the iris image, comprising:
   an image sensor, capturing an image of a scene in front of the image sensor to sequentially generate a plurality of data sequences, wherein each data sequence includes the iris image;
   a digital signal processor, connected to the digital signal processor, selecting a first data sequence among the data sequences as a positioning image and lowering the resolution of the positioning image to generate a low-resolution image; and
   a feature analyzer, connected to the digital signal processor, receiving the low-resolution image, calculating a set of coordinates of the iris image in the low-resolution image, and transmitting the set of coordinates of the iris image to the digital signal processor;
   wherein after receiving the set of coordinates of the iris image, the digital signal processor selects a second data sequence among the data sequences as an image to be processed, and according to the set of coordinates of the iris image, the digital signal processor captures, compresses and encrypts the iris image in the image to be processed to generate and transmit a protected iris image to the feature analyzer;
   wherein the positioning image is included in one data sequence, the image to be processed is included in another data sequence, and the two data sequences are adjacent to each other.

2. The iris image capturing device according to claim 1, wherein when the digital signal processor captures the iris image in the image to be processed according to the set of coordinates of the iris image, the digital signal processor processes the iris image.

3. The iris image capturing device according to claim 2, wherein the digital signal processor processes the iris image based on the exposure or the contrast ratio of the iris image.

4. The iris image capturing device according to claim 1, wherein the resolution of the protected iris image is higher than the resolution of the low-resolution image.

5. The iris image capturing device according to claim 1, wherein the first data sequence is one of the data sequences and the second data sequence is another one of the data sequences.

6. An iris image recognition device, comprising:
   an image sensor, capturing an image of a scene in front of the image sensor to sequentially generate a plurality of data sequences, wherein each data sequence includes an iris image;
   a digital signal processor, connected to the image sensor, selecting a first data sequence among the data sequences as a positioning image, and lowering the resolution of the positioning image to generate a low-resolution image;
   a feature analyzer, connected to the digital signal processor, receiving the low-resolution image, calculating a set of coordinates of the iris image in the low-resolution image, and transmitting the coordinates of the iris image to the digital signal processor; and
   an iris recognizer, connected to the feature analyzer;
   wherein after receiving the coordinates of the iris image, the digital signal processor selects a second data sequence among the data sequences as an image to be processed, and according to the coordinates of the iris image, the digital signal processor captures, compresses and encrypts the iris image in the image to be processed to generate and transmit a protected iris image to the feature analyzer;
   wherein after receiving the protected iris image from the feature analyzer, the iris recognizer decrypts and decompresses the protected iris image to generate a decompressed iris image for the iris recognizer to determine whether the decompressed iris image is an authorized image;
   wherein the positioning image is included in one data sequence, the image to be processed is included in another data sequence, and the two data sequences are adjacent to each other.

7. The iris image recognition device according to claim 6, wherein a unique code mapped to the iris image is stored in the iris recognizer, and when a code mapped to the decompressed iris image is identical to the unique code, the iris recognizer determines that the decompressed iris image is the authorized image.

8. The iris image recognition device according to claim 7, wherein the iris image is unable to be recovered according to the unique code.

9. The iris image recognition device according to claim 6, wherein when the digital signal processor captures the iris image in the image to be processed according to the coordinates of the iris image, the digital signal processor processes the iris image.

10. The iris image recognition device according to claim 9, wherein the digital signal processor processes the iris image based on the exposure or the contrast ratio of the iris image.

11. The iris image recognition device according to claim 6, wherein the resolution of the protected iris image is higher than the resolution of the low-resolution image.

12. The iris image recognition device according to claim 6, wherein the first data sequence is one of the data sequences and the second data sequence is another one of the data sequences.

13. An iris image recognition method, applied to an iris image recognition device, comprising:
- capturing an image of a scene in front of the iris image capturing device to sequentially generate a plurality of data sequences, wherein each data sequence includes an iris image;
- selecting a first data sequence among the data sequences as a positioning image and lowering the resolution of the positioning image to generate a low-resolution image;
- calculating a set of coordinates of the iris image in the low-resolution image;
- selecting a second data sequence among the data sequences as an image to be processed, and according to the set of coordinates of the iris image, capturing, compressing and encrypting the iris image in the image to be processed to generate a protected iris image; and
- decrypting and decompressing the protected iris image to generate a decompressed iris image, and determining whether the decompressed iris image is an authorized image;

wherein the positioning image is included in one data sequence, the image to be processed is included in another data sequence, and the two data sequences are adjacent to each other.

14. The iris image recognition method according to claim 13, wherein a unique code mapped to the iris image is stored in the iris image recognition device, and in the step of determining whether the decompressed iris image is the authorized image, when a code mapped to the decompressed iris image is identical to the unique code, the decompressed iris image is determined as the authorized image.

15. The iris image recognition method according to claim 13, wherein the iris image is unable to be recovered according to the unique code.

16. The iris image recognition method according to claim 13, wherein in the step of capturing the iris image in the image to be processed according to the coordinates of the iris image, the iris image recognition method further comprises:
processing the iris image.

17. The iris image recognition method according to claim 16, wherein in the step of processing the iris image, the iris image is processed based on the exposure or the contrast ratio of the iris image.

* * * * *